(12) United States Patent
Swiss

(10) Patent No.: US 11,717,540 B2
(45) Date of Patent: Aug. 8, 2023

(54) MODIFIED IMMUNE CELLS AND USES THEREOF

(71) Applicant: ISI LIFE SCIENCES, INC., Newport Beach, CA (US)

(72) Inventor: Gerald F. Swiss, San Diego, CA (US)

(73) Assignee: ISI LIFE SCIENCES, INC., Newport Beach, CA (US)

( * ) Notice: Subject to any disclaimer, the term of this patent is extended or adjusted under 35 U.S.C. 154(b) by 513 days.

(21) Appl. No.: 16/645,727

(22) PCT Filed: Sep. 7, 2018

(86) PCT No.: PCT/US2018/050089
§ 371 (c)(1),
(2) Date: Mar. 9, 2020

(87) PCT Pub. No.: WO2019/051317
PCT Pub. Date: Mar. 14, 2019

(65) Prior Publication Data
US 2020/0297765 A1    Sep. 24, 2020

Related U.S. Application Data

(60) Provisional application No. 62/555,445, filed on Sep. 7, 2017, provisional application No. 62/585,472, filed on Nov. 13, 2017.

(51) Int. Cl.

| | | |
|---|---|---|
| *C07D 401/14* | (2006.01) | |
| *A61K 31/192* | (2006.01) | |
| *A61K 31/395* | (2006.01) | |
| *A61K 31/454* | (2006.01) | |
| *A61K 35/17* | (2015.01) | |
| *A61K 47/55* | (2017.01) | |
| *A61K 39/395* | (2006.01) | |
| *C07D 475/04* | (2006.01) | |
| *C07K 16/22* | (2006.01) | |
| *C07K 19/00* | (2006.01) | |
| *C12N 5/078* | (2010.01) | |
| *C07D 257/00* | (2006.01) | |

(52) U.S. Cl.
CPC .......... *A61K 35/17* (2013.01); *A61K 39/3955* (2013.01); *A61K 47/551* (2017.08); *C07D 257/00* (2013.01); *C07D 475/04* (2013.01); *C07K 16/22* (2013.01); *C07K 19/00* (2013.01); *C12N 5/0634* (2013.01)

(58) Field of Classification Search
CPC .. C07D 401/14; A61K 31/192; A61K 31/395; A61K 31/454
See application file for complete search history.

(56) References Cited

U.S. PATENT DOCUMENTS

2004/0132993 A1    7/2004  Shetty
2008/0300165 A1    12/2008 Poznansky et al.

OTHER PUBLICATIONS

Bridger et al. (1995) "Synthesis and Structure-Activity Relationships of Phenylenebis(methylene) Linked Bis-Tetraazamacrocycles That Inhibit HIV Replication. Effects of Macrocyclic Ring Size and Substituents on the Aromatic Linker", Journal of Medicinal Chemistry, 38:366-378.
Jacobson et al. (2009) "64Cu-AMD3100—A novel imaging agent for targeting chemokine receptor CXCR4", Bioorganic & Medicinal Chemistry, 17(4):1486-1493.
Liu et al. (2016) "Effectiveness of AMD3100 in treatment of leukemia and solid tumors: from original discovery to use in current clinical practice", Experimental Hematology & Oncology, 5(19):11 pages.
Poty et al. (Jan. 2015) "New AMD3100 Derivatives for CXCR4 Chemokine Receptor Targeted Molecular Imaging Studies: Synthesis, anti-HIV-1 Evaluation and Binding Affinities", Dalton Transactions, 44:5004-5016.
Rosenkilde et al. (Jan. 2004) "Molecular Mechanism of AMD3100 Antagonism in the CXCR4 Receptor Transfer of Binding Site to the CXCR3 Receptor", Journal of Biological Chemistry, 279(4):3033-3041.

*Primary Examiner* — Bruck Kifle
(74) *Attorney, Agent, or Firm* — Mintz, Levin, Cohn, Ferris, Glovsky & Popeo, P.C.

(57) ABSTRACT

Disclosed are modified T-cells so that the modified T-cells are capable of penetrating the fugetactic wall generated by tumors, including solid mass tumors, as well as imparting tumor specific targeting for these modified T-cells.

17 Claims, No Drawings

MODIFIED IMMUNE CELLS AND USES THEREOF

CROSS-REFERENCES TO RELATED APPLICATIONS

This application claims the benefit of U.S. Provisional Application Nos. 62/555,445, filed Sep. 7, 2017; and 62/585,472, filed Nov. 13, 2017; each of which is incorporated herein by reference in entirety and for all purposes.

FIELD

This disclosure provides for modified immune cells such as T-cells and NK cells so that the modified cells are capable of penetrating the fugetactic wall generated by a tumor, including solid mass tumors, as well as imparting tumor specific targeting for these modified cells.

BACKGROUND

It is art recognized that CXCL12 (aka SDF-1) is a ligand for CXCR4. CXCR4 receptors are expressed on many cellular surfaces including T-cells such as $T_{eff}$ and $T_{reg}$ cells, NK cells and the like. Under normal conditions, certain immune cells are able to follow a concentration gradient of CXCL12 that provides the necessary directional guidance so that these immune cells are delivered to sites of infection, inflammation, etc. However, as a defense mechanism, tumors, e.g., solid mass tumors, overexpress the cytokine CXCL12. Such creates a fugetactic wall around the tumor as the overexpression of CXCL12 sufficiently saturates the CXCR4 receptors on the such immune thereby "blinding" the directional guidance.

Poznansky, US Pub. No. 2008/0300165, discloses that AMD3100 (1-[[4-(1,4,8,11-tetrazacyclotetradec-1-ylmethyl)phenyl]methyl]-1,4,8,11-tetrazacyclotetra-decane) acts to inhibit solid mass tumor fugetaxis by interfering with the binding of CXCL12 to CXCR4 on T-cells. While such interference permits the T-cells to penetrate through the fugetactic wall, these T-cells are still compromised in having directional guidance. US Pub. No. 2008/0300165 is incorporated herein by reference in its entirety.

Accordingly, there is a need to provide immune cells such as NK-cells and T-cells and, in particular, $T_{eff}$-cells, with the ability to penetrate through the fugetactic wall of tumors, e.g., solid mass tumors while also providing tumor specific targeting to these immune cells.

SUMMARY

This disclosure provides for modified immune cells wherein these cells are modified by complexation with an AMD3100 conjugate containing a ligand for a tumor specific receptor on a cancer cell or a ligand that is overexpressed on a cancer cell as compared to normal cells.

This disclosure provides for a combination of both tumor specific targeting to immune cells such as NK cells and T-cells while allowing the immune cells to penetrate through the tumor's fugetactic wall. Specifically, this invention provides for (1-[[4-(1,4,8,11-tetrazacyclotetradec-1-ylmethyl)phenyl]methyl]-1,4,8,11-tetrazacyclotetra-decane) derivatives wherein said derivatives comprise targeting moieties covalently bound thereto either directly or through a linker.

In particular, in one embodiment, this disclosure provides for modified immune cells wherein said cells are modified either ex vivo or in vivo. When modified ex vivo, these cells are then delivered to the patient. Specifically, immune cells are modified ex vivo by contact with a conjugate of AMD3100 so that the conjugate retains the ability to mitigate the fugetactic effect of solid mass tumors while imparting tumor specific targeting to the modified T-cells. When delivered in vivo, the modified AMD3100 compounds containing the tumor targeting agent will complex with endogenous T-cells so as to impart both tumor targeting to the T-cells as well as to mitigate the fugetactic effect of cancer cells.

This combination of properties addresses a need in the art where AMD3100 complexation with immune cells, e.g., natural killer (NK) cells or T-cells, allows these immune cells to pass through the tumor's fugetactic wall but does not impart tumor specific targeting. On the other hand, the recent advances in CAR-T cells provides for tumor specific targeting but an inability to penetrate through the fugetactic effect of a tumor, e.g., solid mass tumor. Moreover, the efficacy of CAR-T cells are unpredictable with certain clinical studies terminated due to the death of healthy volunteers.

In one aspect, the conjugate can be administered to any patient having a tumor that expresses/overexpresses a particular antigen or the folate receptor. Unlike CAR-T therapy, which requires that a new population of CAR-T cells be created for every patient, this technology allows for off-the-shelf treatment of cancers that express the relevant antigen/receptor. Furthermore, and without being bound by theory, it is expected that the conjugates of the present technology improve the therapeutic effect of cancer immunotherapies (in particular, therapeutic antibodies) by targeting T cells to the cancer cells and/or reducing the fugetactic effect of a cancer to allow better access of T cells to a tumor.

This disclosure provides for a combination of both tumor specific targeting to immune cells such as NK cells and T-cells while allowing the immune cells to penetrate through the tumor's fugetactic wall. Specifically is provided (1-[[4-(1,4,8,11-tetrazacyclotetradec-1-ylmethyl)phenyl]methyl]-1,4,8,11-tetrazacyclotetra-decane) conjugates wherein said conjugates comprise 1 to 2 folic or pteroic acid molecules covalently bound thereto either directly or through a linker. Without being limited by any theory, it is contemplated that immune cells complexed with the AMD3100 conjugates of this invention are able to pass through the fugetactic wall surrounding the tumor and into the tumor microenvironment where the immune cells are cytotoxic to the tumor cells.

In one embodiment, there is provided a conjugate comprising AMD3100-(1-[[4-(1,4,8,11-tetrazacyclotetradec-1-ylmethyl)phenyl]methyl]-1,4,8,11-tetrazacyclotetra-decane) bound either directly to a targeting agent or indirectly via a linker that links AMD3100 to the targeting agent.

Chemically, AMD is a bicyclam ring system where each ring system binds to separate portions of the CXCR4 receptor. Molecular modeling suggests that one cyclam ring interacts with Asp(171) in TM-IV, whereas the other ring is sandwiched between the carboxylic acid groups of Asp(262) and Glu(288) from TM-VI and —VII, respectively. Metal ion binding in the cyclam rings of AMD3100 increased its dependence on Asp(262) and provided a tighter molecular map of the binding site. J Biol Chem. 2004 Jan. 23; 279(4):3033-41.

In view of the criticality of each bicyclam ring system, conjugates of AMD3100 as described herein are made from the phenyl group central to the molecule. As this phenyl group does not participate in binding to CXCR4, it is available for conjugation as per below.

In one embodiment, there is provided a conjugate comprising folic or pteroic acid bound to AMD3100-(1-[[4-(1, 4,8,11-tetrazacyclotetradec-1-ylmethyl)phenyl]methyl]-1,4,8,11-tetrazacyclotetra-decane) either directly via conversion of its alpha or gamma carboxyl group via a suitable bond such as an amide bond where the amide bond if formed by reaction of a carboxyl group of folic or pteroic acid with an amine group of AMD3100. In another embodiment, folic or pteroic acid is bound to AMD3100 via a linker moiety that is bound to either a nitrogen atom or to carbon atom of the phenyl ring.

In one embodiment, the compounds are represented by a conjugate of formula I:

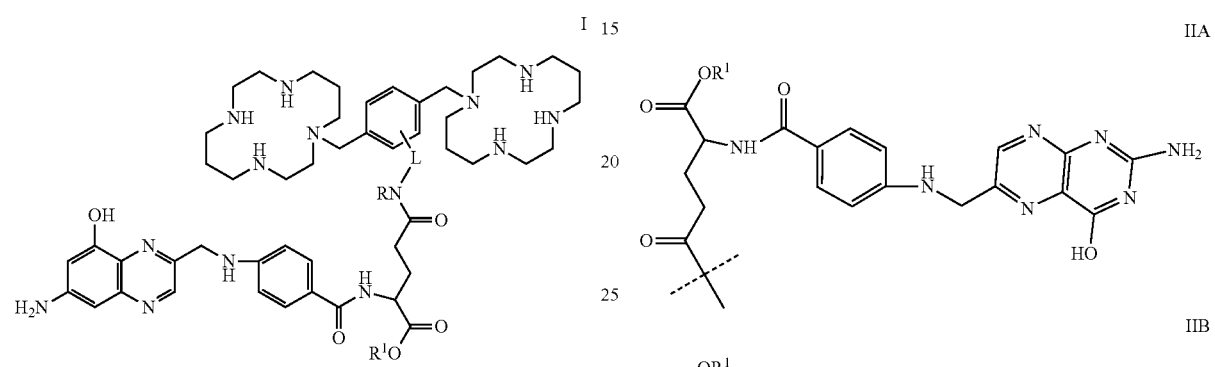

where R and $R^1$ are independently hydrogen or $C_1$-$C_6$ alkyl,

L is a bond or a linker group having from 1 to 30 atoms selected from carbon moiety (e.g., methylene, $CHCH_3$, carbonyl, vinyl, acetylene, etc.), NH, $NR^2$ (where $R^2$ is $C_1$-$C_4$ alkyl), O, S, S(O), and $S(O)_2$, or a pharmaceutically acceptable salt and/or solvate thereof.

In one embodiment, the compounds are represented by a conjugate of formula IA:

IA where $R^1$ is hydrogen or $C_1$-$C_6$ alkyl,

L is a bond or a linker group having from 1 to 30 atoms selected from a carbon moiety (e.g., methylene $CHCH_3$, carbonyl, vinyl, acetylene, etc.), NH, $NR^2$ (where $R^2$ is $C_1$-$C_4$ alkyl), O, S, S(O), and $S(O)_2$, or a pharmaceutically acceptable salt and/or solvate thereof.

In one embodiment, there is provided a conjugate of formula II:

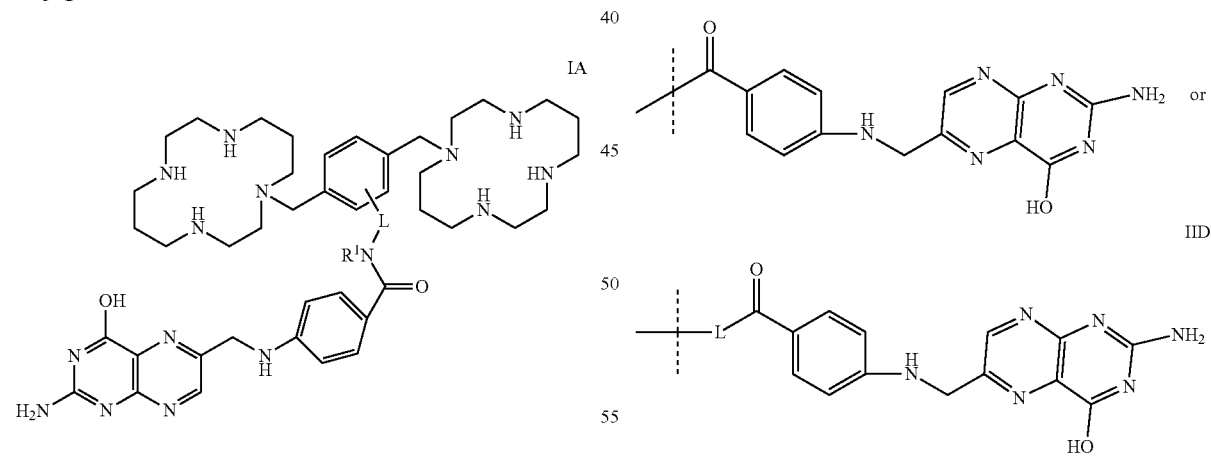

where one or two of the NH groups of said compound are replaced with NR where R is selected from the group of:

IIA

IIB

IIC or

IID where $R^1$ is hydrogen or $C_1$-$C_6$ alkyl,

L is a bond or a linker group having from 1 to 30 atoms selected from carbon moiety (e.g., methylene, carbonyl, vinyl, acetylene, etc.), NH, $NR^2$ (where $R^2$ is $C_1$-$C_4$ alkyl), O, S, S(O), and $S(O)_2$, or a pharmaceutically acceptable salt and/or solvate thereof.

Folic acid, also known as Vitamin B-9, is well known to target tumors, e.g., solid mass tumors that overexpress the folate receptor. Such overexpression arises as folic acid is required for nucleic acid synthesis and rapidly dividing cancer cell require more nucleic acid than normal cells. Solid mass cancers known to overexpress folate receptors include ovarian, cervical, breast, renal, non-small cell lung, brain, colorectal and epithelial cancers.

Pteroic acid, which is folic acid without the glutamic acid residue, also binds to folate receptors.

By incorporating targeting moieties onto AMD3100, subsequent complexation of AMD3100 with immune cells such as T-cells enhances the ability of these cells to traverse through the tumor's fugetactic wall while also providing these cells with tumor specific targeting—namely targeting the tumor specific receptors or folate receptor on cancer cells, or receptors that are overexpressed by cancer cells.

Accordingly, in one embodiment are provided immune cells modified by complexation with a sufficient amount of a compound of formula I, IA, II, IIA, IIB, IIC, IID, IIIA, IIIB, and/or IV so as to enhance the ability of the modified immune cells to traverse through the tumor's fugetactic wall while also providing these cells with tumor specific targeting.

In another embodiment are provided immune cells having bound thereto folic or pteroic acid either directly or via a linker so as to impart tumor specific targeting to said cells and wherein said bound cells are complexed with a sufficient amount of AMD3100 to enhance the penetration of said so modified cells through the tumor's fugetactic wall.

In one embodiment, the immune cells are T-cells, including e.g., naïve T cells, $T_{eff}$ cells and/or $T_{reg}$ cells.

In one embodiment, the immune cells are NK cells such as NK-92 cells.

In one of its method aspects, this disclosure relates to a method for imparting tumor specific targeting to immune cells while also enhancing the ability of these cells to traverse through the tumor's fugetactic wall which method comprises:
  providing for immune cells ex vivo; and
  modifying said immune cells by incorporating AMD3100 and folic or pteroic acid onto said cells wherein said folic or pteroic acid is either covalently linked to AMD3100 or said folic or pteroic acid are covalently bound to said cells.

In one embodiment, the immune cells are T-cells comprising naïve T cells, e.g., naïve CD8 T cells, $T_{eff}$ cells and/or $T_{reg}$ cells.

In one embodiment, the immune cells are NK cells such as NK-92 cells.

In another of its method aspects, this disclosure provides for a method for treating a patient suffering from a cancer, e.g., solid mass tumor that overexpresses folate receptor said method comprising administering to said patient an effective amount of a compound described herein optionally as part of a pharmaceutical composition.

In one embodiment, the compounds of this invention are represented by a compound of formula IV:

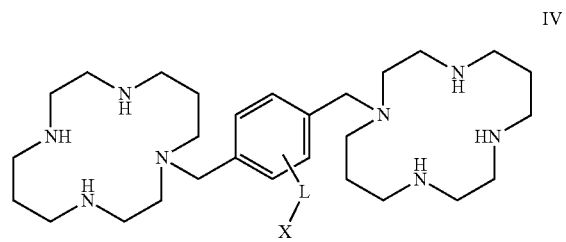

IV where X is a ligand to a tumor specific receptor or a receptor that is overexpressed by cancer cells; and L is a bond or a linker group having from 1 to 30 atoms selected from carbon (e.g., methylene, carbonyl, vinyl, acetylene, etc.), NH, $NR^2$ (where $R^2$ is $C_1$-$C_4$ alkyl), O, S, S(O), and $S(O)_2$, or a pharmaceutically acceptable salt and/or solvate thereof.

Numerous commercially available chemotherapeutic agents are ligands for tumor specific receptors or for receptors overexpressed by cancer cells. These ligands bind to such receptors and inhibit their function thereby imparting chemotherapeutic properties.

Examples of such chemotherapeutic agents include those that bind to the HER-2 receptor that is overexpressed in about 15-25% of all breast cancers. Chemotherapeutic agents that target HER-2 include lapatinib, Afatinib, ASD8931, AST1306, AEE788, Canertinib, CP27,714, CUDC101, TAK285, Dacomitinib, Pelitinib, AC480, and the like.

Similarly, chemotherapeutic agents targeting oestrogen receptors are likewise used to treat breast cancer. Such agents include, by way of example only, faslodex, raloxifene, tamoxifen, toremifen and idoxifene. See, e.g., www.ncbi.nlm.nih.gov/pmc/articles/PMC2852629/.

In one embodiment, the targeting agent on the compounds of formula I include those that target HER-2 receptors, folic acid receptors, and oestrogen receptors. These targeting agents are preferably attached via a linker moiety as described above.

In one embodiment, the immune cells are T-cells comprising $T_{eff}$ cells and/or $T_{reg}$ cells.

In one embodiment, the immune cells are NK cells such as NK-92 cells.

In one aspect is provided a method for imparting tumor specific targeting to immune cells while also enhancing the ability of these cells to traverse through the tumor's fugetactic wall, which method comprises:
  binding a ligand for a tumor specific receptor or a ligand for a receptor overexpressed on cancer cells as compared to normal cells to AMD3100; and
  contacting T-cells with said modified AMD3100 compounds under conditions wherein said modified AMD3100 complexes with the CXCR4 receptors on said T-cells.

In one embodiment, the immune cells are T-cells comprising $T_{eff}$ cells and/or $T_{reg}$ cells.

In one embodiment, the immune cells are NK cells such as NK-92 cells.

In aspect is provided a method for treating a patient suffering from a tumor, e.g., solid mass tumor, that expresses a tumor specific receptor or a receptor that is overexpressed by said tumor, wherein said method comprises:
  a) contacting T-cells with a compound of formula IV optionally as part of a pharmaceutical composition so as to form a complex between CXCR4 receptors on said T-cells and said compound so as to form modified T-cells; and
  b) contacting said modified T-cells with said tumor.

DETAILED DESCRIPTION

This disclosure provides for compositions and methods for treating cancer.

However, prior to discussing this disclosure in further detail, the following terms will be defined.

Definitions

As used herein, the following definitions shall apply unless otherwise indicated. Further, if any term or symbol used herein is not defined as set forth below, it shall have its ordinary meaning in the art.

As used herein and in the appended claims, singular articles such as "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

The term "fugetaxis" or "fugetactic" refers to the ability of an agent to repel (or chemorepel) an eukaryotic cell with migratory capacity.

The term "immune cells" refers to cells of hematopoietic origin that are involved in the specific recognition of antigens. Immune cells include antigen presenting cells (APCs), such as dendritic cells or macrophages, B cells, T-cells, NK cells such as NK-92 cells, etc. T-cells include $T_{eff}$ cells and $T_{reg}$ cells.

Folic acid refers to vitamin B-9 and has the structure:

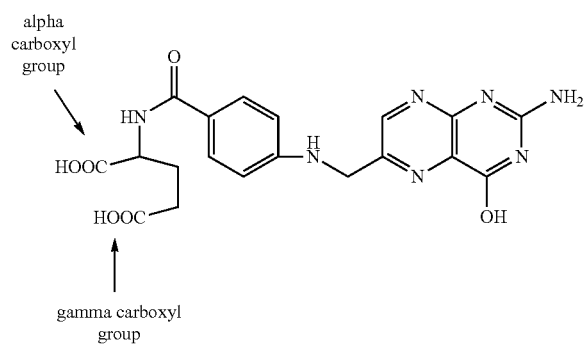 [SMILES: Nc1nc(O)c2nc(CNc3ccc(C(=O)NC(CCC(=O)O)C(=O)O)cc3)cnc2n1]

where the alpha and gamma carboxyl groups are as defined therein.

Pteroic acid refers to the compound:

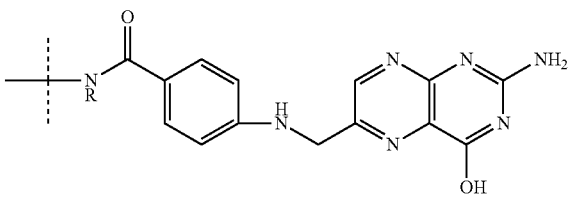

where R is hydrogen or $C_1$-$C_6$ alkyl.

Stereoisomers of compounds (also known as optical isomers) include all chiral, d,l stereoisomeric, and racemic forms of a structure, unless the specific stereochemistry is expressly indicated. Thus, compounds used herein include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners, and these stereoisomers are all within the scope of this disclosure.

The compounds described herein may exist as solvates, especially hydrates. Hydrates may form during manufacture of the compounds or compositions comprising the compounds, or hydrates may form over time due to the hygroscopic nature of the compounds. Compounds described herein may exist as organic solvates as well, including DMF, ether, and alcohol solvates among others. The identification and preparation of any particular solvate is within the skill of the ordinary artisan of synthetic organic or medicinal chemistry.

"Subject" refers to a mammal. The mammal can be a human or non-human animal mammalian organism.

"Tautomer" refers to alternate forms of a compound that differ in the position of a proton, such as enol-keto and imine-enamine tautomers, or the tautomeric forms of heteroaryl groups containing a ring atom attached to both a ring —NH— moiety and a ring=N— moiety such as pyrazoles, imidazoles, benzimidazoles, triazoles, and tetrazoles. All tautomeric forms of the compounds are encompassed herein.

"T effector cells" or "$T_{eff}$ cells" refers to T cells having cytotoxic activity towards a tumor cell.

Synthesis

The compounds described herein can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and P. G. M. Wuts, *Protecting Groups in Organic Synthesis*, Third Edition, Wiley, New York, 1999, and references cited therein.

If the compounds described herein contain one or more chiral centers, such compounds can be prepared or isolated as pure stereoisomers, i.e., as individual enantiomers or d(l) stereomers, or as stereoisomer-enriched mixtures. All such stereoisomers (and enriched mixtures) are included within the scope of this disclosure, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures, or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989), Organic Reactions, Volumes 1-40 (John Wiley, and Sons, 1991), March's Advanced Organic Chemistry, (John Wiley, and Sons, 5$^{th}$ Edition, 2001), and Larock's Comprehensive Organic Transformations (VCH Publishers Inc., 1989).

First, phenyl substituted derivatives of AMD3100 are known in the art. See, for example, Poty, et al., Dalton Transactions, 2015, 44, 5004-5016 which article is incorporated herein by reference in its entirety. In that article, the following derivatives of AMD3100 are described:

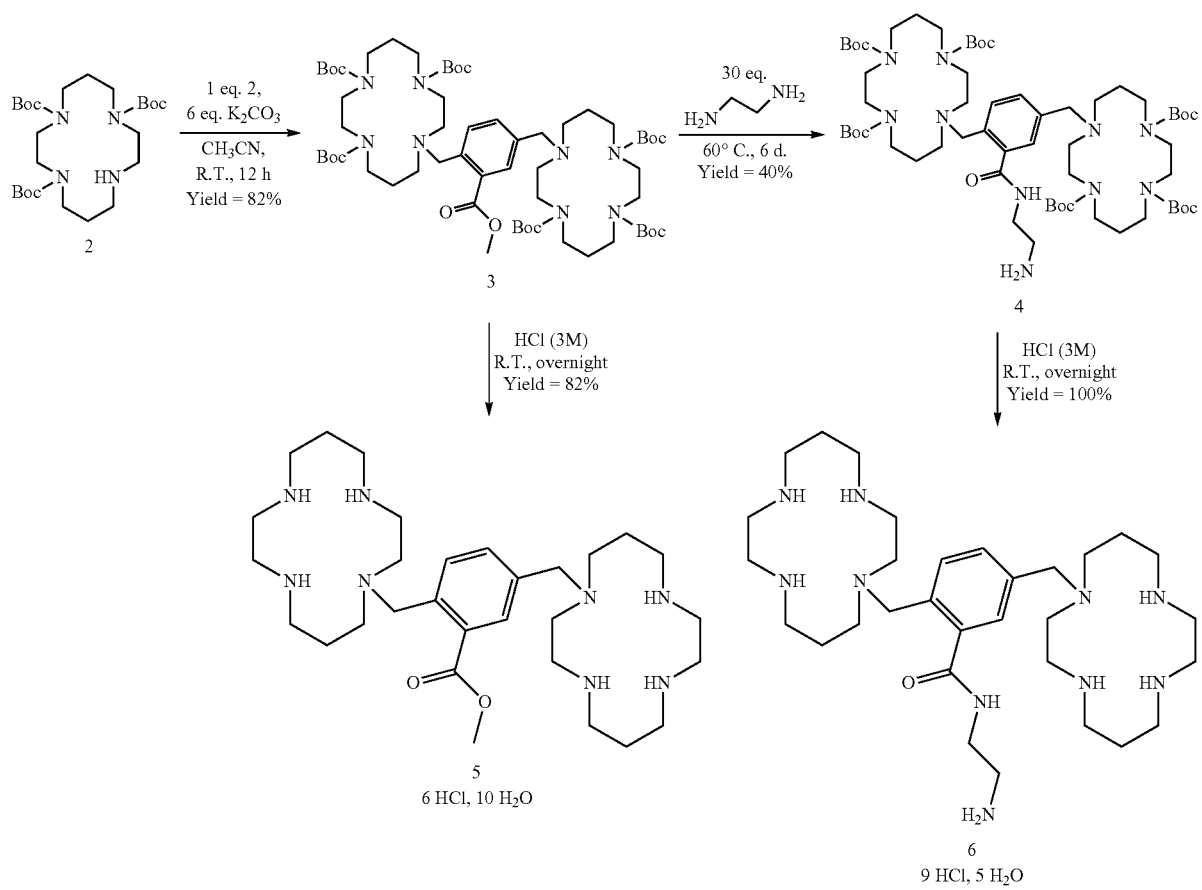

Further derivation of these compounds can be readily conducted. For example, the methyl ester, compound 5, can be converted to the corresponding carboxylic acid and used to directly bind to a corresponding reactive group on a ligand as described above. Alternatively, the carboxyl group can be reduced to a hydroxyl group to react with corresponding reactive functional groups on the ligand which groups are well known in the art.

In another embodiment, the carboxylic acid can be used as a starting point for linker formation. For example, the use of a PEGylated linker will result in an ester bond. Such PEG groups include those of the formula: $HOCH_2CH_2(OCH_2CH_2O)_nH$ where n is an integer from 0 to 100. In another embodiment, the carboxylic acid derived from compound 5 can also be used to form an amide linker such as those derived amino acids, Jeffamines (e.g., $(H_2NCH_2CH_2(OCH_2CH_2)pNH_2$ where p is an integer from 1 to 100).

The free amino group of compound 6 is likewise available to either directly bind to a corresponding reactive functional group on the ligand as described above converted into a suitable linker by conventional methods.

In all cases, once conversion is made, the Boc protecting groups are removed by conventional methods.

For direct conjugation of folic acid to AMD3100, commercially available AMD3100 is combined with folic anhydride under conventional amidation conditions to form compounds of this disclosure where attachment is to any available nitrogen of AMD3100.

In order to limit conjugation of a single folic acid to AMD3100, a solution of folic anhydride is added dropwise to a solution of excess AMD3100 under conditions that favor formation of the monoamide. This reaction is illustrated below (L=bond) and the folic anhydride is a literature preparation.

Scheme 1 below illustrates this reaction and depicts two possible products having a single folic acid moiety that can be prepared. Note that as AMD3100 is symmetrical, any amidation on the left ring is equivalent to amidation to the same nitrogen on the right ring. As there are three different secondary amines, three different amide products are possible.

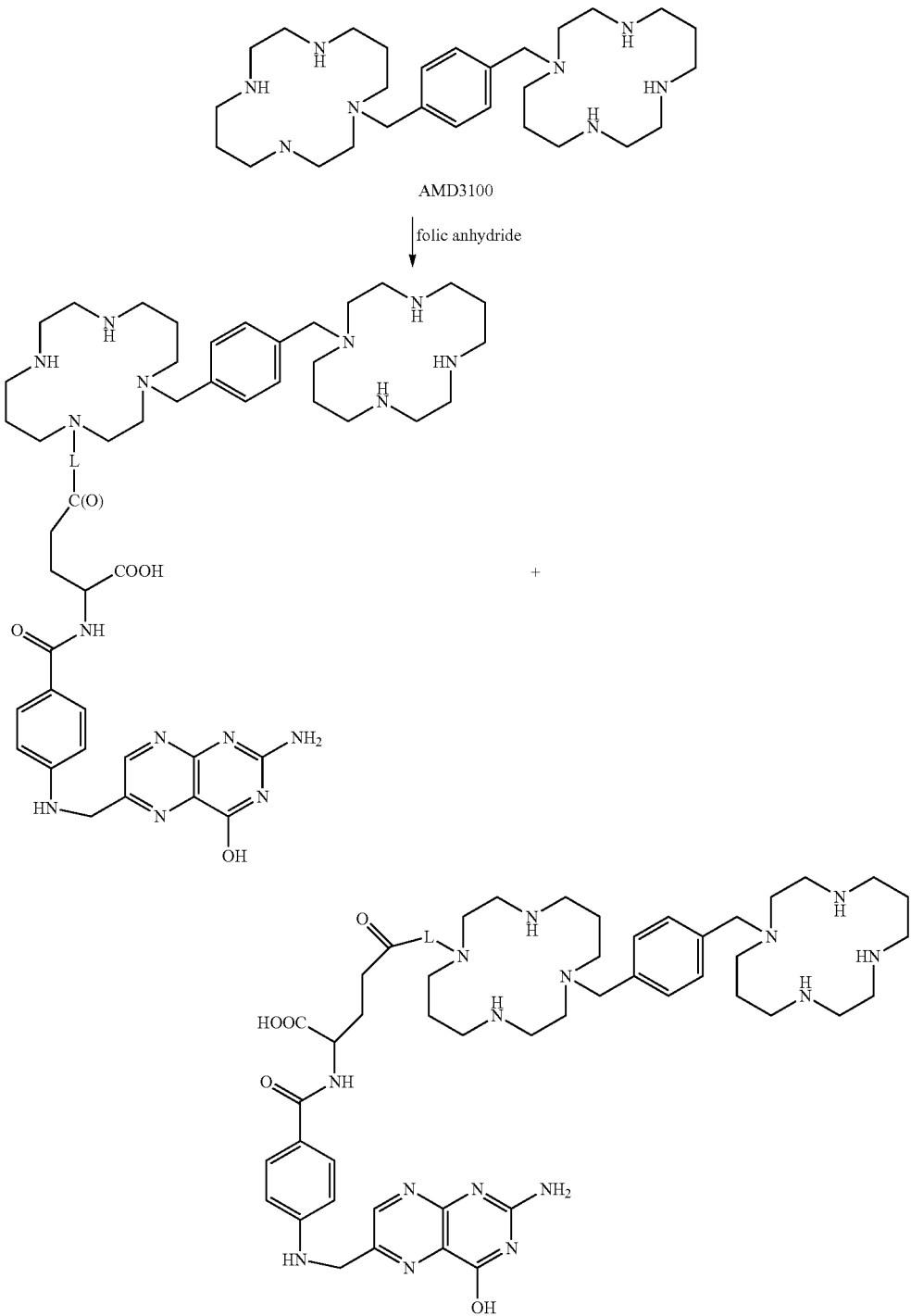

-continued

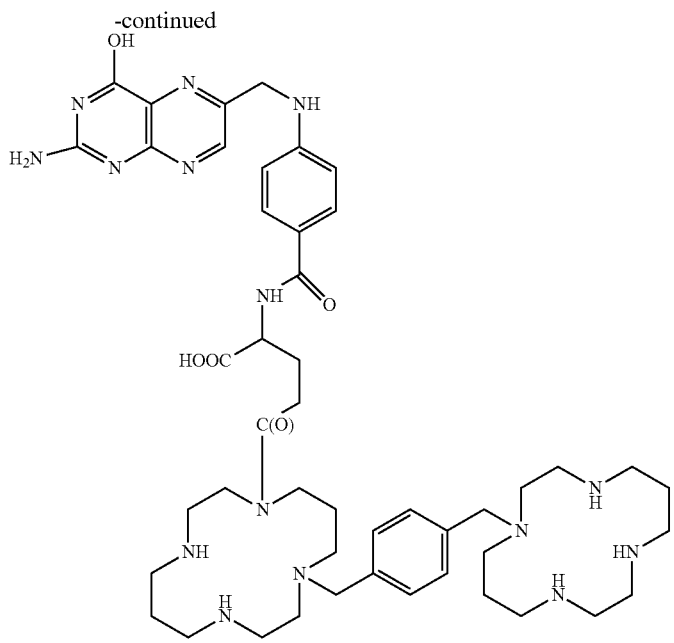

When L is a linker, conventional reactions can be used to link folic acid to AMD3100. For example, folic anhydride can be opened with ethanolamine to provide for the following compound:

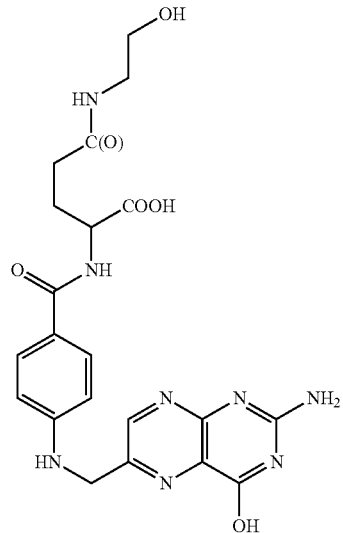

The conversion of the primary alcohol to a chloroformate can be achieved by contacting the above compound with triphosgene and triethylamine as per the literature with protection of other reactive functional groups as necessary.

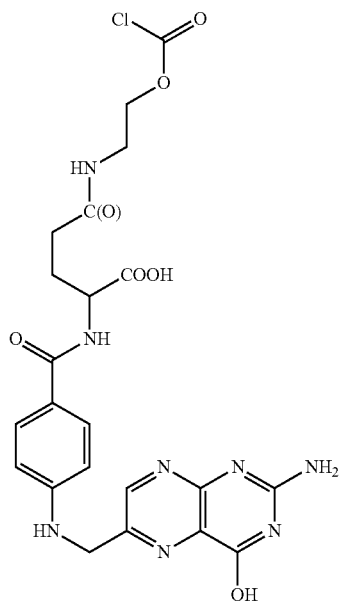

Dropwise addition of a solution containing the chloroformate to AMD3100 will provide for the conjugate containing a linker. Other linkers can be prepared from amino acids such as serine, threonine, and the like.

Still other linkers can be made by using a carboxyl protected amino acid such as $NH_2$—R—COOPg where R is $C_1$-$C_{20}$ alkylene, $C_2$-$C_{20}$ alkenylene, $C_2$-$C_{20}$ alkynylene, polyoxy $C_2$-$C_3$ alkylene comprising 2-30 oxyalkylene units, $C_4$-$C_{30}$ polyoxyalkylene, and the like. Pg is a conventional carboxyl protecting group.

An embodiment of this disclosure is a conjugate of formula III:

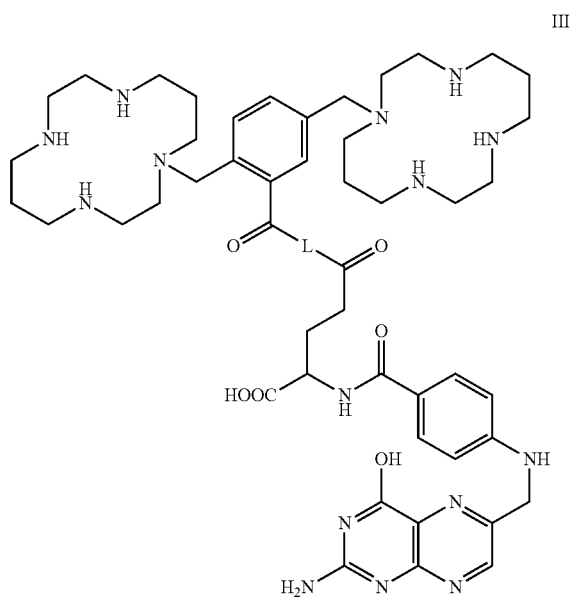

III

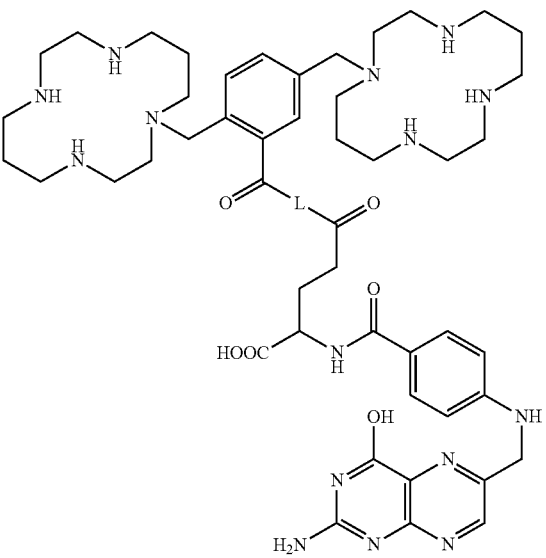

where L is a bond or a linker group having from 1 to 30 atoms selected from a carbon moiety (e.g., methylene, CHCH$_3$, carbonyl, vinyl, acetylene, etc.), NH, NR$^2$ (where R$^2$ is C$_1$-C$_4$ alkyl), O, S, S(O), and S(O)$_2$, or a pharmaceutically acceptable salt and/or solvate thereof.

An embodiment of this disclosure is a conjugate of formula IIIA:

where L is as defined herein.

Formation of the folic or pteroic acid residue on the phenyl ring proceeds via an intermediate disclosed by Poty, et al., Dalton Transactions, 2015, 44, 5004-5016 which article is incorporated herein by reference in its entirety. Poty, et al. disclose

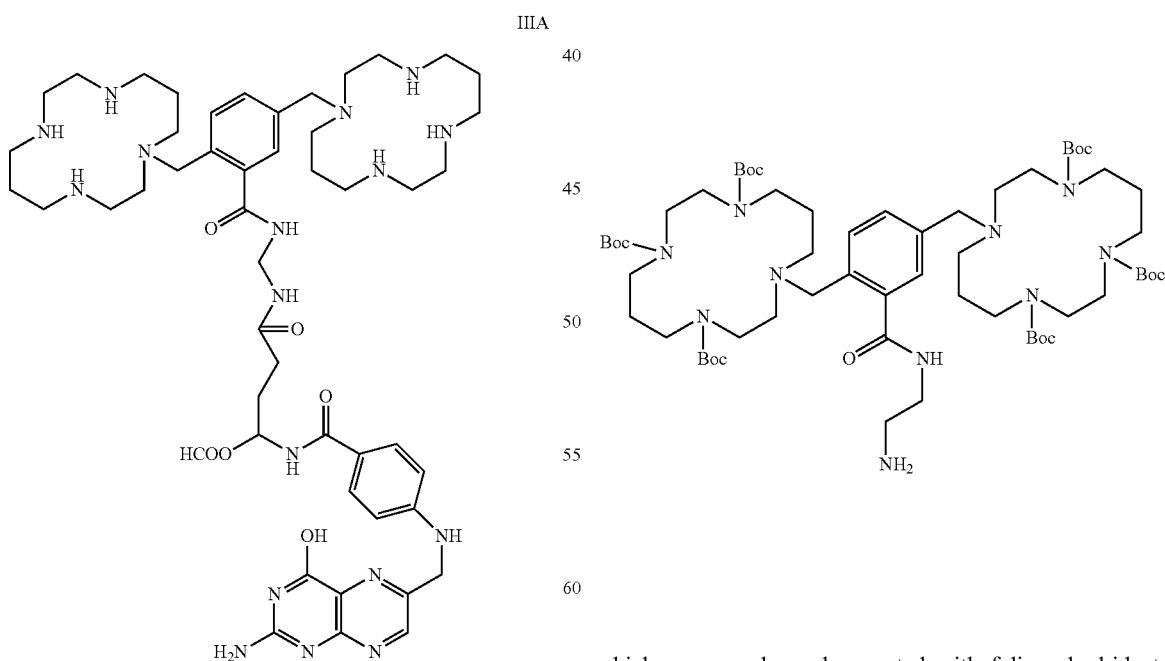

IIIA

It is understood that the linker (—NHCH$_2$CH$_2$NH—) group can be replaced by other linkers to provide for a compound of the formula:

which compound can be reacted with folic anhydride to provide for amidation of the gamma carboxyl group of folic acid. Subsequent removal of the tert-butyloxycarbonyl (Boc) protecting groups with trifluoroacetic acid or hydrogen chloride provides for the compound:

IIIB

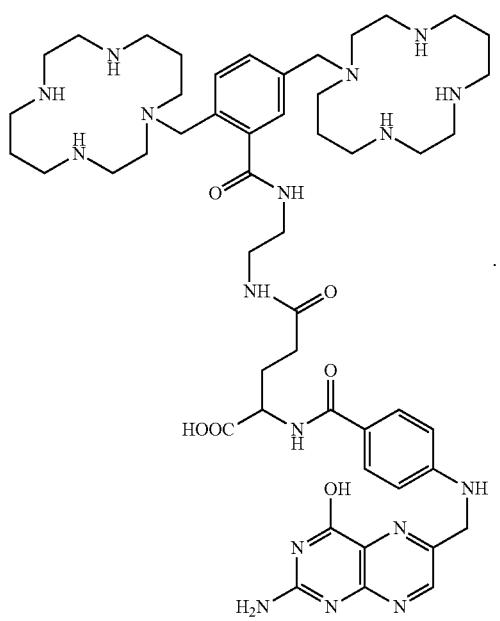

Alternative Embodiment

In an alternative embodiment, covalent attachment of folic or pteroic acid to extracted T-cells can be accomplished by conventional amidation using the primary amine group of lysine found of the surface of T-cells. Subsequent addition of an effective amount of AMD3100 complexes with the modified T-cells to inhibit binding of CXCL12 thereby inhibiting the fugetactic effect of excess CXCL12 against such T-cells. The order of addition is not critical.

In another alternative embodiment, the tumor targeting agent is a monoclonal antibody that recognizes a tumor-associated epitope. Examples of tumor targeting agents are antibodies that target VEGF (a tumor-derived antigen) such as bevacizumab; CD20 (e.g., rituximab); or HER2 (e.g., trastuzumab, pertuzumab). The particular antibody used is not critical, so long as it binds to a tumor-associated or tumor-derived antigen. In this embodiment, coupling of the antibody to AMD3100 derivative is demonstrated here and below. Such complexation provides for a well-known antibody with tumor targeting capacity and therapeutic properties which can be administered by conventional means, e.g., IV injection. Preferably, administration of the conjugate is directly to the patient, e.g., via IV administration.

Complexation

AMD3100 is known to complex with the CXCR4 receptors on immune cells. See, Poty, et al., supra. Complexation of AMD3100 with CXCR4 receptors is believed to involve amino acids $Asp^{171}$ and $Asp^{262}$ of the receptor. Modification of AMD3100 have demonstrated that such modified compounds retain their ability to complex with the CXCR4 receptors. However, to date, complexation was conducted to enhance the potency of AMD3100 and not to impart tumor specific targeting.

Utility

The conjugates described herein are capable of modifying T-cells so as to be tumor target specific and to enhance their penetration though the fugetactic wall of tumors. The conjugates are employed in sufficient concentration such that at least about 20% or about 30% or about 40% or about 50% or about 60% or about 70% or about 80% or about 90% of the CXCR4 receptors on the treated T-cells are unable to bind CXCL12. The so treated T-cells are administered to the patient in an amount sufficient to treat a tumor, e.g., a solid mass tumor, e.g. a tumor that overexpresses folate receptors.

In one embodiment, a compound of formula I is used in combination with AMD3100 so that only a sufficient number of ligands to tumor receptors are present. For example, one could employ a ratio of a compound of formula I to AMD3100 as follows: 1:99; 3:97; 5:95, 7:93; 10:90; 15:85; 20:80, 25:75; 30:70; 35:65; 40:60; 45:55 and 1:1.

The immune cell-conjugate complexes described herein can be formed ex vivo and then administered to the patient. Alternatively, the complexes can be formed in vivo by administering the conjugate to the patient (e.g., by IV administration) such that the conjugate complexes with circulating T cells. The amount of the composition so administered is predicated on the amount of antibody or tumor-targeting agent deemed acceptable by the attending physician, the amount of such commercially available antibodies for administration to a patient is well known in the art.

As to folic acid and pteroic acid, these compounds are well known (folic acid is vitamin B9). The use of these compounds as tumor targeting agents is predicated upon over-expression of the folic acid receptor by many cancers, including ovarian, colorectal, cervical, breast, epithelial, and other cancers.

EXAMPLES

Example 1—Synthesis of Folic Acid—Serine—AMD3100 Conjugate

Scheme 1

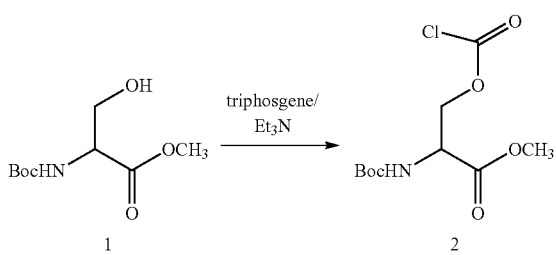

-continued
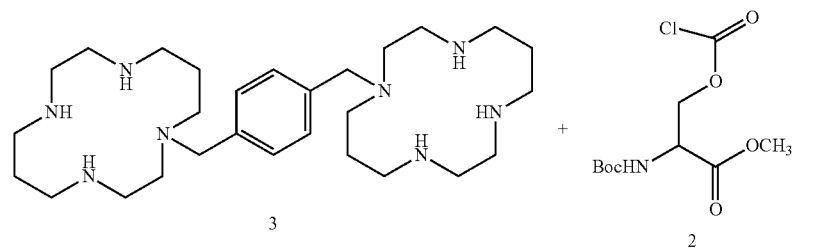
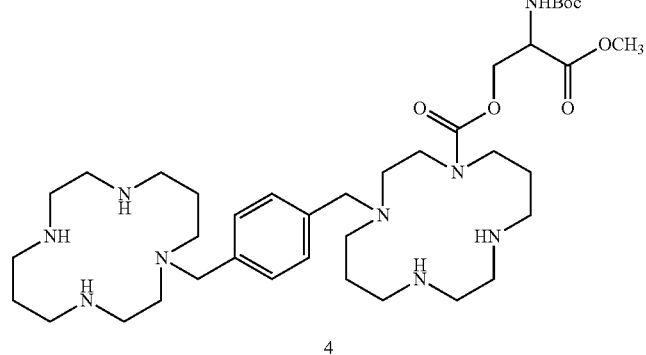
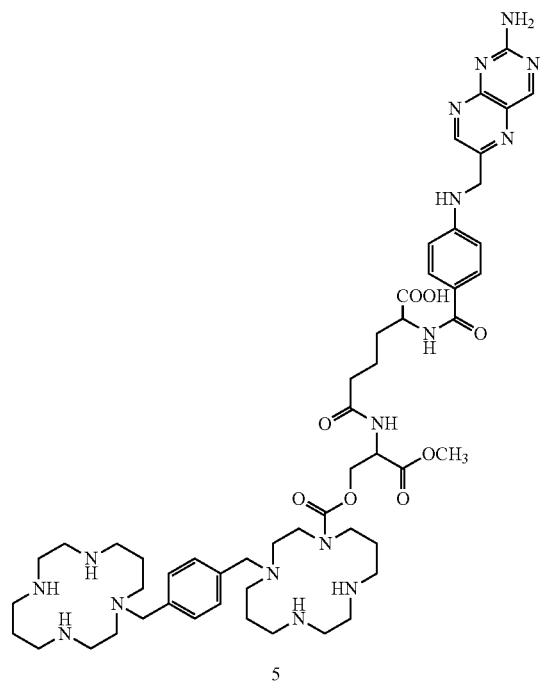

As per the above, commercially available N-(t-butoxycarbonyl) serine methyl ester (Sigma Aldrich, St. Louis, Mo., USA), serine methyl ester AMD3100, compound 1, is treated under conventional conditions with at least a stoichiometric amount and preferably an excess of commercially available triphosgene in the presence of triethylamine so as to provide for the chloroformate, compound 2.

Commercially available AMD3100 (1-[[4-(1,4,8,11-tetrazacyclotetradec-1-ylmethyl)phenyl]methyl]-1,4,8,11-tetrazacyclotetradecane), compound 3, is dissolved into methylene chloride containing an excess of triethylamine and the solution is cooled and then maintained at about 0° C. Approximately 0.3 equivalents of chloroformate, compound 2, is also dissolved in methylene chloride and added dropwise to the cooled solution while stirring vigorously. The use of 0.3 equivalent of compound 3 is to minimize multiple additions of compound 2 to compound 3. After reaction completion, unreacted chloroformate is quenched by conventional methods.

The reaction mixture can then be purified by conventional methods such as chromatography, distillation, precipitation, high performance liquid chromatography (HPLC), and the like to provide for compound 4.

Removal of the N-Boc group proceeds via conventional methods and then coupling of the amino group with folic anhydride by methods well known in the art provides for the corresponding amide.

Finally, optional deacylation of the methyl ester follows conventional methods to provide for compound 5.

Compounds prepared by the above synthesis include compounds of formula IA, IB and IC as described herein.

Still other compounds that can be prepared include those starting with pteroic acid rather than folic acid. Such compounds are prepared as per above and provide, for example, compounds of formula IIE, IIF, and IIG.

IIE

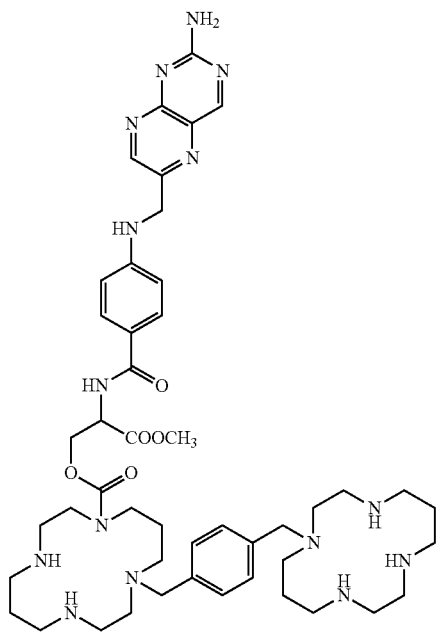

IIF

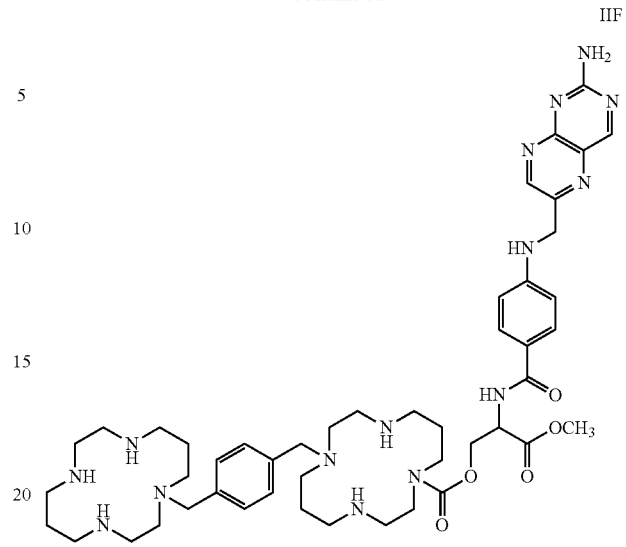

IIG

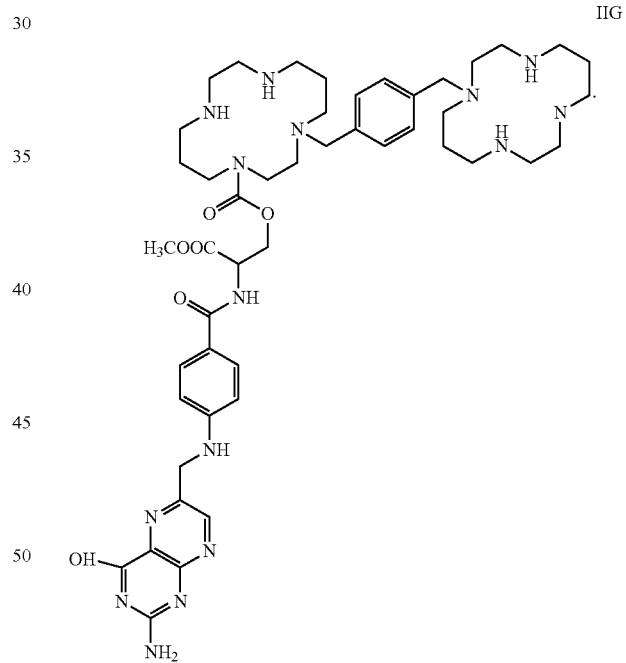

Example 2—AMD3100 Bound to Rituximab

Rituximab (commercially available as RITUXAN®) contains over 35 aspartic and glutamic acid residues in its heavy chain. For illustrative purposes only, the side chain of these residues are illustrated below as HOOC—(CH$_2$)$_n$ where n is 1 for aspartic acid and 2 for glutamic acid. Rituximab is known to bind to the CD20 epitope of B cells including aberrant B cells.

The reaction scheme to couple compound 4 (above) to rituximab is shown in the following scheme:

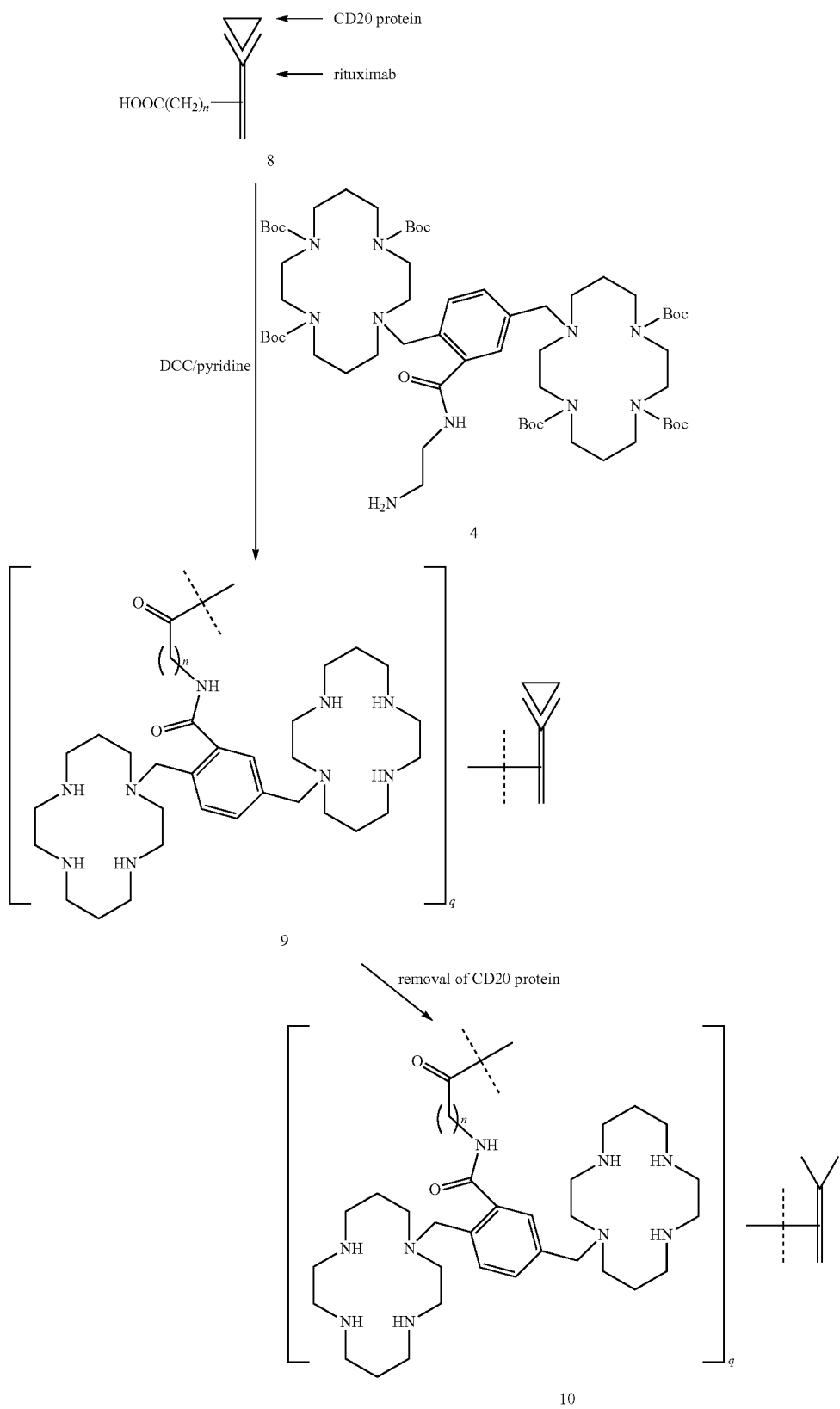
In the above scheme, rituximab is combined with commercially available recombinant CD20 protein under conditions that provide for compound 8. This step is to ensure that in the next step, reaction of the antibody with compound 4 does not occur in the binding site of the antibody. The CD20 protein may be attached to a solid support for ease of handling and elution of the AMD3100-rituximab complex after formation.

Compound 8 is then combined with compound 4 in a manner similar to Example 1 above to form a covalent amide linkage between the aspartic acid residues (n=1) and the glutamic acid residues (n=2) on rituximab where q is an integer from 1 to 35 and preferably 1 to 25 and more preferably 10 to 20. After removal of the Boc groups, compound 9 is obtained. Conventional removal of the CD20 protein from compound 9 provides for the title compound 10.

The above examples are merely illustrative of the technology described herein and do not limit or otherwise restrict the disclosure which is set forth herein and in the appended claims.

The invention claimed is:

1. A conjugate having a folic acid or pteroic acid covalently bound to (1-[[4-(1,4,8,11-tetrazacyclotetradec-1-ylmethyl)phenyl] methyl]-1,4,8,11-tetrazacyclotetra-decane) optionally through a linker.

2. The conjugate of claim 1, wherein the folic acid or pteroic acid is bound to a nitrogen atom of -(1,4,8,11-tetrazacyclotetradec-1-ylmethyl)phenyl] methyl]-1,4,8,11-tetrazacyclotetra-decane) optionally through a linker.

3. The conjugate of claim 2, wherein the folic acid or pteroic acid is bound to a nitrogen atom of -(1,4,8,11-tetrazacyclotetradec-1-ylmethyl)phenyl] methyl]-1,4,8,11-tetrazacyclotetra-decane) via an amide bond.

4. The conjugate of claim 1, wherein the folic acid or pteroic acid is bound to a carbon atom of the phenyl moiety of (1-[[4-(1,4,8,11-tetrazacyclotetradec-1-ylmethyl)phenyl] methyl]-1,4,8,11-tetrazacyclotetra-decane) optionally through a linker.

5. A conjugate of formula IIA, IIB, IIC, or IID:

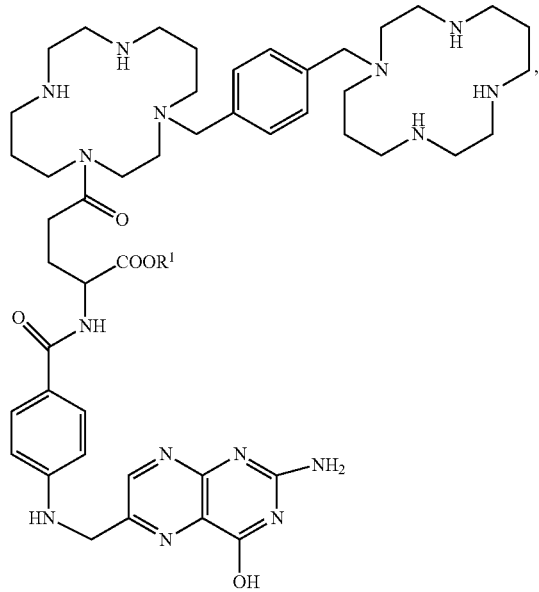

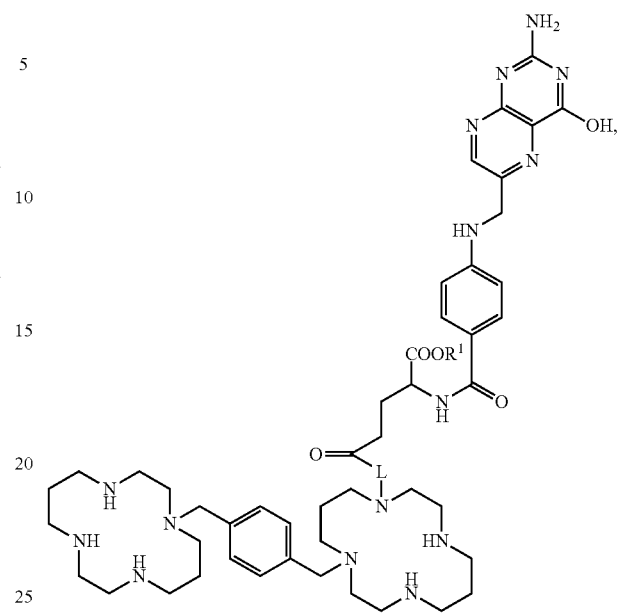

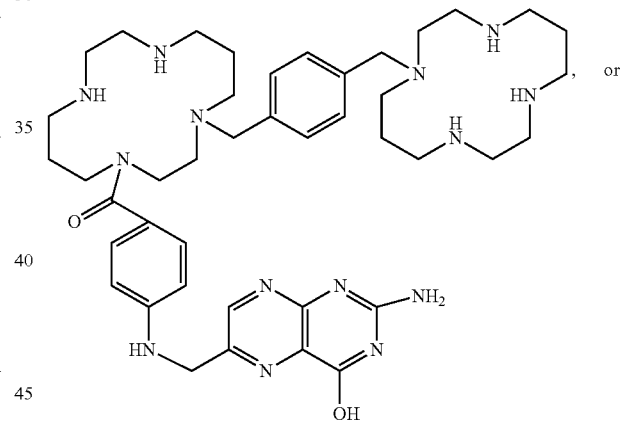

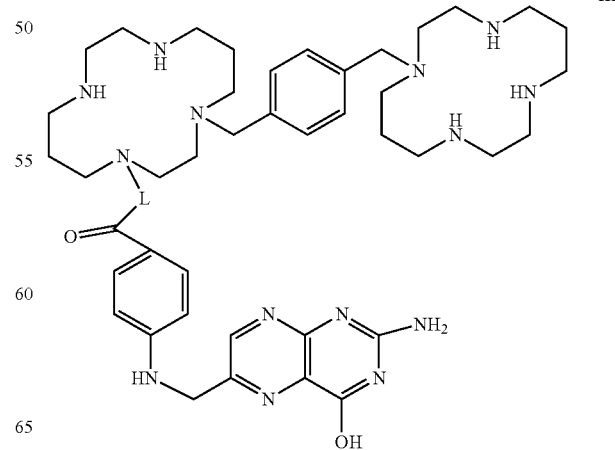

where R¹ is hydrogen or $C_1$-$C_6$ alkyl, where L is a linker group selected from $C_1$-$C_{30}$ straight chain or branched alkylene, $C_2$-$C_{30}$ alkenylene, and $C_2$-$C_{30}$ alkynylene, $C_2$-$C_{30}$ oxyalkylene, $C_4$-$C_{30}$ polyoxyalkene, wherein said alkylylene, alkenylene or alkynylene is optionally substituted with a —C(O)OH, —$CO_2CH_3$, NH, $NR^2$, O, S, S(O), and $S(O)_2$, wherein $R^2$ is $C_1$-$C_4$ alkyl, or a pharmaceutically acceptable salt thereof.

6. A conjugate of formula IIE, IIF, or IIG:

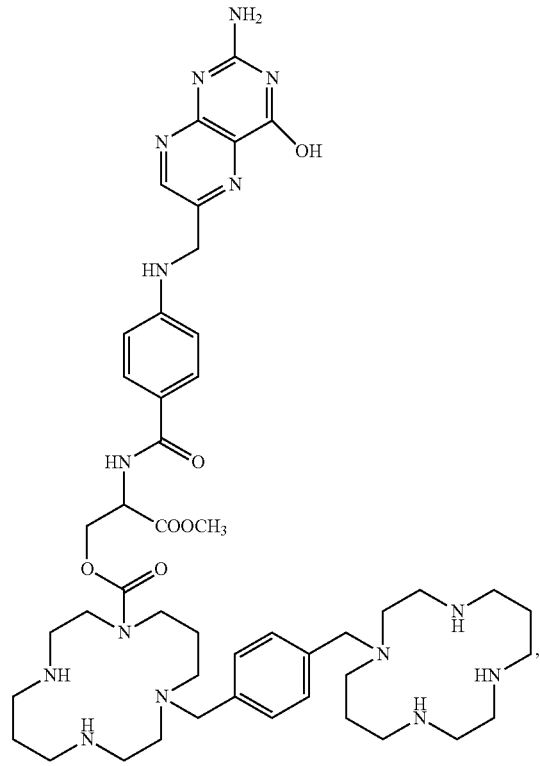

IIE

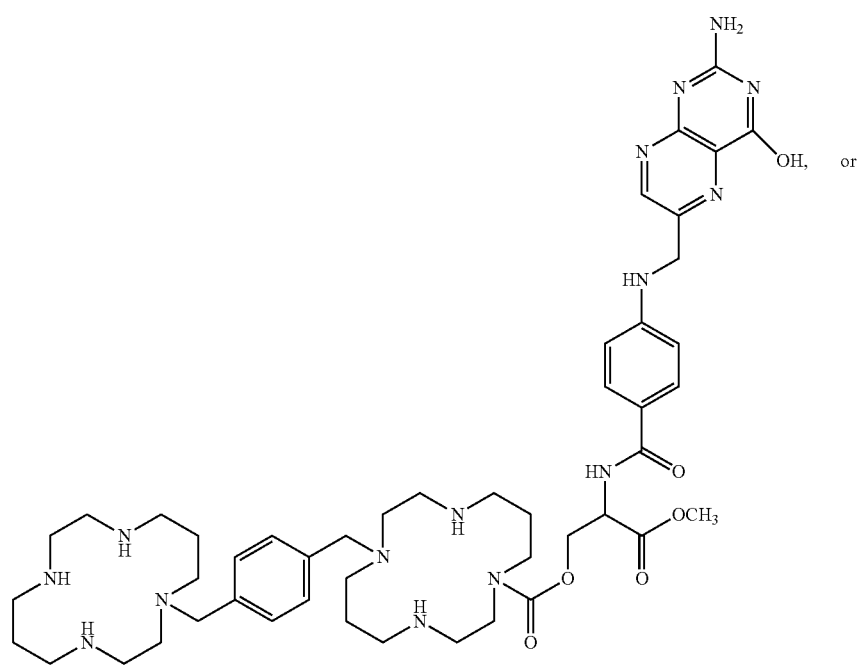

IIF, or

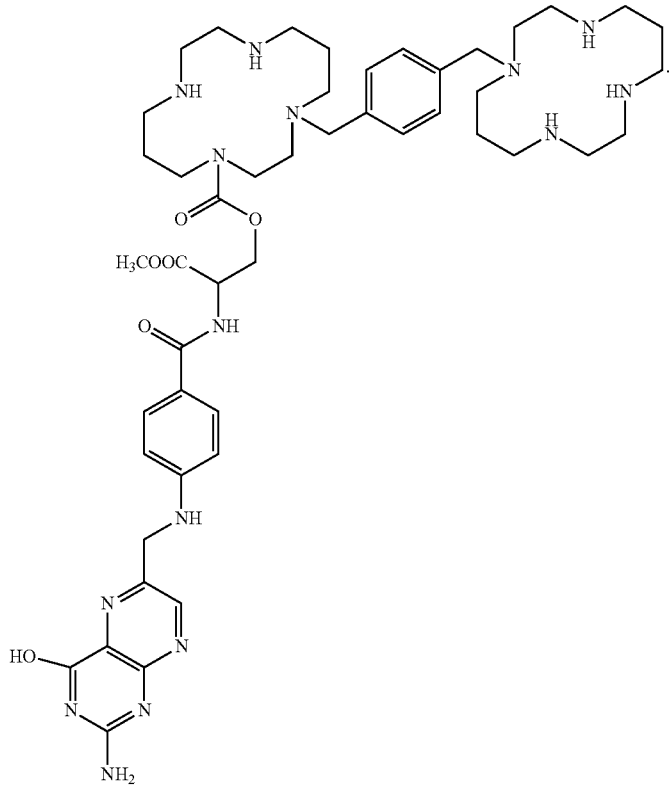

IIG

7. A conjugate of formula IIIA:

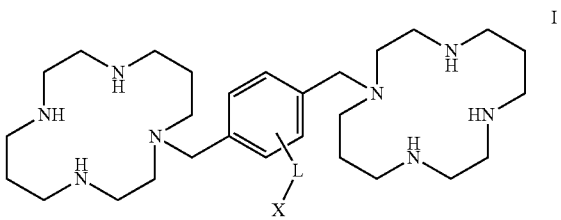

IIIA

8. A compound of formula I:

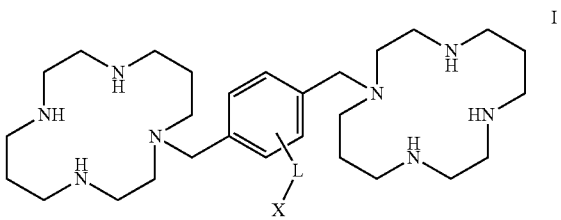

I where X is a folic acid or pteroic acid ligand to a tumor specific receptor or a receptor that is overexpressed by cancer cells; and L is a bond or a linker group s selected from $C_1$-$C_{30}$ straight chain or branched alkylene, $C_2$-$C_{30}$ alkenylene, and $C_2$-$C_{30}$ alkynylene, $C_2$-$C_{30}$ oxyalkylene, $C_4$-$C_{30}$ polyoxyalkene, wherein said alkylylene, alkenylene or alkynylene is optionally substituted with a —C(O)OH, —CO$_2$CH$_3$, NH, NR$^2$, O, S, S(O), and S(O)$_2$, wherein R$^2$ is $C_1$-$C_4$ alkyl, or a pharmaceutically acceptable salt-thereof.

9. A conjugate of the formula:

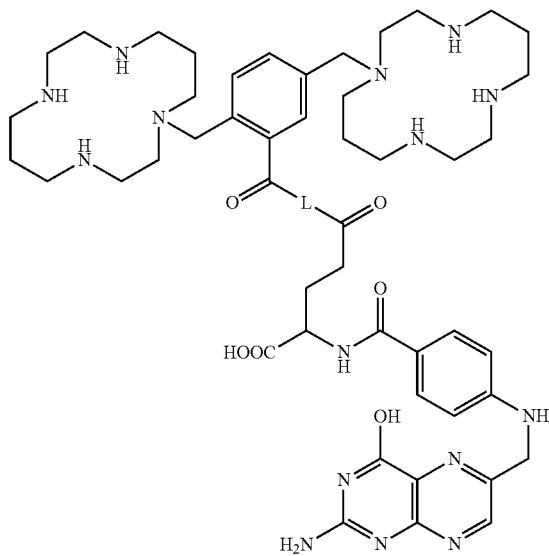

where L is a linker group selected from $C_1$-$C_{30}$ straight chain or branched alkylene, $C_2$-$C_{30}$ alkenylene, and $C_2$-$C_{30}$ alkynylene, $C_2$-$C_{30}$ oxyalkylene, $C_4$-$C_{30}$ polyoxyalkene, wherein said alkylylene, alkenylene or alkynylene is optionally substituted with a —C(O)OH, —$CO_2CH_3$, NH, $NR^2$, O, S, S(O), and $S(O)_2$, wherein $R^2$ is $C_1$-$C_4$ alkyl, or a pharmaceutically acceptable salt thereof.

10. The conjugate of claim 1, wherein the folic acid is covalently bound to (1-[[4-(1,4,8,11-tetrazacyclotetradec-1-ylmethyl)phenyl] methyl]-1,4,8,11-tetrazacyclotetra-decane) optionally through a linker.

11. The conjugate of claim 1, wherein the pteroic acid is covalently bound to (1-[[4-(1,4,8,11-tetrazacyclotetradec-1-ylmethyl)phenyl] methyl]-1,4,8,11-tetrazacyclotetra-decane) optionally through a linker.

12. The conjugate of claim 2, wherein the folic acid which is bound to a nitrogen atom of -(1,4,8,11-tetrazacyclotetradec-1-ylmethyl)phenyl] methyl]-1,4,8,11-tetrazacyclotetradecane) optionally through a linker.

13. The conjugate of claim 2, wherein the pteroic acid which is bound to a nitrogen atom of -(1,4,8,11-tetrazacyclotetradec-1-ylmethyl)phenyl] methyl]-1,4,8,11-tetrazacyclotetra-decane) optionally through a linker.

14. The conjugate of claim 3, wherein the folic acid which is bound to a nitrogen atom of -(1,4,8,11-tetrazacyclotetradec-1-ylmethyl)phenyl] methyl]-1,4,8,11-tetrazacyclotetradecane) via an amide bond.

15. The conjugate of claim 3, wherein the pteroic acid which is bound to a nitrogen atom of -(1,4,8,11-tetrazacyclotetradec-1-ylmethyl)phenyl] methyl]-1,4,8,11-tetrazacyclotetra-decane) via an amide bond.

16. The conjugate of claim 4, wherein the folic acid which is bound to a carbon atom of the phenyl moiety of (1-[[4-(1,4,8,11-tetrazacyclotetradec-1-ylmethyl)phenyl]methyl]-1,4,8,11-tetrazacyclotetra-decane) optionally through a linker.

17. The conjugate of claim 4, wherein the pteroic acid which is bound to a carbon atom of the phenyl moiety of (1-[[4-(1,4,8,11-tetrazacyclotetradec-1-ylmethyl)phenyl] methyl]-1,4,8,11-tetrazacyclotetra-decane) optionally through a linker.

* * * * *